US011705316B2

United States Patent
Trede et al.

(10) Patent No.: US 11,705,316 B2
(45) Date of Patent: *Jul. 18, 2023

(54) MASS SPECTROMETRIC DETERMINATION OF TISSUE STATES

(71) Applicant: Bruker Daltonics GmbH & Co. KG, Bremen (DE)

(72) Inventors: Dennis Trede, Bremen (DE); Jan Hendrik Kobarg, Bremen (DE); Stefan Schiffler, Bremen (DE); Klaus Steinhorst, Bremen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,594

(22) Filed: May 18, 2022

(65) Prior Publication Data

US 2022/0277941 A1 Sep. 1, 2022

Related U.S. Application Data

(63) Continuation of application No. 16/888,137, filed on May 29, 2020, now Pat. No. 11,367,600.

(30) Foreign Application Priority Data

Jun. 3, 2019 (DE) .............................. 102019114829

(51) Int. Cl.
| | | |
|---|---|---|
| *H01J 49/00* | (2006.01) | |
| *G01N 33/483* | (2006.01) | |
| *B01D 59/44* | (2006.01) | |
| *G01N 27/64* | (2006.01) | |

(52) U.S. Cl.
CPC .......... *H01J 49/0004* (2013.01); *B01D 59/44* (2013.01); *G01N 27/64* (2013.01); *G01N 33/483* (2013.01)

(58) Field of Classification Search
CPC .. H01J 49/0004; H01J 49/004; H01J 49/0036; H01J 49/00; H01J 49/26; G01N 33/483; G01N 27/64; G01N 2560/00; G01N 2570/00; G01N 33/5091; G01N 27/622; G01N 33/4833; G01N 1/30; G01N 33/50; B01D 59/44
See application file for complete search history.

(56) References Cited

U.S. PATENT DOCUMENTS

| | | | |
|---|---|---|---|
| 9,304,106 B1 * | 4/2016 | Park ........................ | H01J 49/06 |
| 10,192,715 B2 * | 1/2019 | Renner ................ | G01N 27/622 |
| 10,458,944 B2 * | 10/2019 | Räther ............... | H01J 49/0063 |
| 10,615,022 B2 * | 4/2020 | Böhm ................... | H01J 49/403 |
| 10,886,115 B2 * | 1/2021 | Deininger ........... | H01J 49/0004 |
| 11,047,828 B2 * | 6/2021 | Räther .................... | H01J 49/40 |
| 11,062,891 B2 * | 7/2021 | Boskamp ............... | G16B 40/10 |
| 11,367,600 B2 * | 6/2022 | Trede ................. | G01N 33/5091 |

(Continued)

*Primary Examiner* — David A Vanore
(74) *Attorney, Agent, or Firm* — Benoît & Côté

(57) ABSTRACT

The invention relates to a method for the determination and visualization of the spatial distribution of tissue states of a tissue sample, wherein a mass/mobility map is acquired at each of a plurality of sample sites of the tissue sample, the signal heights at each sample site are determined at characteristic signal positions in the corresponding mass/mobility map, from which a tissue state for each sample site is calculated with the aid of a mathematical/statistical classification algorithm, and the spatial distribution of the tissue states calculated for the sample sites is represented graphically.

20 Claims, 5 Drawing Sheets

(56) References Cited

U.S. PATENT DOCUMENTS

| | | | | |
|---|---|---|---|---|
| 2011/0098198 A1* | 4/2011 | Trede | ............ | G06T 7/0012 |
| | | | | 506/10 |
| 2016/0163523 A1* | 6/2016 | Maass | ............ | H01J 49/164 |
| | | | | 702/19 |
| 2018/0103935 A1* | 4/2018 | Pringle | ............ | A61B 10/0233 |
| 2020/0381229 A1* | 12/2020 | Trede | ............ | H01J 49/004 |

* cited by examiner

MASS SPECTROMETRIC DETERMINATION OF TISSUE STATES

BACKGROUND OF THE INVENTION

Field of the Invention

The invention relates to the determination and visualization of the spatial distribution of tissue states in tissue samples, for example histological tissue sections, from spatially resolved mass spectrometric signals.

Description of the Related Art

Histology is the science of human, animal and plant tissues, particularly their structure and function. A histological classification of a tissue is equivalent to the determination of the tissue state, which can relate to the type and differentiations of the tissue, bacterial and parasitic pathogens in the tissue, the disease state of the tissue, or any other change compared to a normal state. In the following, the term "histology" also includes the analysis of tissue samples for disease states ("histopathology"). The disease states of tissue relate to inflammatory diseases, metabolic diseases and the detection of tumors, especially the differentiation between benign and malignant forms of tumor.

In routine histological work, the tissue states are determined by means of optical images of tissue sections, which are acquired with the aid of microscopes or scanners. The tissue sections used are only a few micrometers thick and are stained to enhance the contrast in the optical images and make the structures in the tissue sections visible. Until now, histology has predominantly been a morphological diagnostic method because the tissue states have been determined using the appearance and staining characteristics of tissue and cell structures. Since normal practice is to acquire an optical image of a complete tissue section, it is possible and usual to determine tissue states at different sites on the tissue section, i.e. with spatial resolution.

The tissue state is also reflected, at the molecular level, in concentration patterns of biological substances, such as proteins, nucleic acids, lipids or sugars (glycans). A molecular pattern can result when biological substances in certain tissue states are underexpressed or overexpressed. In particular, proteins, for example, can be present which have been modified in a characteristic way by post-translational modifications, e.g. by phosphorylation, glycolyzation or silanization. In recent years, the search for substances which are characteristic of diseases (so-called biomarkers) has developed into a field of clinical research which has attracted a great deal of attention. To this end, the biological substances in body fluids (e.g. blood, urine or spinal fluid) or homogenized tissue samples are typically separated into fractions by solid phase extraction or chromatographic separation methods before being subjected to a mass spectrometric analysis. The mass spectra measured exhibit a more or less complex signal pattern, which usually originates from peptides, proteins and lipids.

The mass spectrum of a tissue sample contains a large amount of molecular information with a plurality of signals, wherein the tissue state is usually established not by an individual signal, but only by a signal pattern. There are many different mathematical/statistical classification algorithms which can be used to determine the state of a tissue sample from the high-dimensional signal pattern of a measured mass spectrum, e.g. neuronal networks (linear vector quantization (LVQ), neural gas (NG), self-organizing map (SOM)), support vector machines (SVM), genetic algorithms for cluster analysis, principal component analysis (PCA), decision trees or nearest neighbor classifiers (k nearest neighbor).

Before the tissue state of a tissue sample can be determined using a classification algorithm, mass spectra of many tissue samples which have different tissue states and whose tissue state is known in each case are first measured and analyzed to establish whether the classification algorithm actually allows the tissue states to be distinguished on the basis of the measured mass spectra. If settings for the parameters of the classification algorithm are found which enable tissue states in the mass spectra to be differentiated, these parameter settings can be used to assign a mass spectrum of a tissue sample under investigation to one of the classes, and thus to determine the tissue state of the tissue sample under investigation.

Some classification algorithms allow statements to be made about which signals of the mass spectra are relevant for a classification. Principal component analysis (PCA), for example, is utilized to undertake a reduction to those signals which have a major impact on the variance of the high-dimensional signal patterns, and thus often contain a large amount of information. With the so-called supervised classification algorithms, for example support vector machines, it is additionally necessary for each mass spectrum to be assigned to a previously known class (e.g. diseased or healthy) in a training phase of the algorithm, i.e. for these "training spectra" to bear a label.

In recent years, a type of imaging mass spectrometry has become established which can analyze histological tissue sections rather than homogenized tissue samples, preferably with MALDI time-of-flight mass spectrometers (MALDI=matrix assisted laser desorption/ionization). Various methods and devices which can be used for the preparation of tissue sections on MALDI sample supports are known from the patent specifications DE 10 2006 019 530 B4 and DE 10 2006 059 695 B3. To this end, a matrix solution in the form of small droplets is applied by vibration nebulization to a tissue section, for example. The solvent vaporizes and the matrix substance crystallizes together with substances extracted from the tissue section. As a rule, a raster scan method according to Caprioli (U.S. Pat. No. 5,808,300 A) is used to measure spatially resolved MALDI mass spectra. Parts of the tissue section can also be imaged by ion-optical means (Luxembourg et al., Analytical Chemistry, 76(18), 2004, 5339-5344: "High-Spatial Resolution Mass Spectrometric Imaging of Peptide and Protein Distributions on a Surface"). In both cases, a corresponding mass map of the tissue section results from the signals of each mass interval which is resolved in the mass spectra. The molecular information of the tissue section is therefore available with spatial resolution.

The patent specification DE 10 2004 037 512 B4 discloses that mass spectra are measured with spatial resolution for a tissue section, and that from each of the spatially resolved mass spectra (or portions thereof), a spatially resolved tissue state is calculated at the corresponding site on the tissue section. It is not a tissue state of a (homogenized) tissue sample which is determined here, but a state map of the tissue section. The spatially resolved tissue states, as pixels of the state map, are calculated with the aforementioned mathematical/statistical classification algorithms. The information from the many measured mass maps of the tissue section is merged in a single state map, and thus becomes easy for the user to access visually.

The spatially resolved mass spectra of a tissue section under investigation can be used to specify the parameters of the classification algorithm before the tissue states in other areas of the tissue section under investigation are determined. With supervised classification algorithms, however, this requires that the tissue state of the spatially resolved mass spectra which are used to train the classification algorithm must be known in advance. But the parameter settings of the classification algorithm may also be available in a pre-evaluated form, e.g. from previous analyses of spatially resolved mass spectra of other similar tissue sections or analyses of mass spectra of homogenized, similar tissue samples.

A platform for imaging mass spectrometry which can be used to directly image a tissue at ambient pressure is known from the publication WO 2016/142696 A1. An imaging method here involves automatic sampling at a large number of sample sites, wherein an aerosol, smoke or vapor is generated from the tissue sample at the sample sites. Mass spectra and/or mobility spectra are acquired at the sample sites, and these spectra are assigned to the respective sample site. The mass spectra and/or mobility spectra obtained are used to design, train or improve and apply a classification model.

Unfortunately, the large number of different substances in a tissue sample and the associated plurality of signals mean that it is often difficult to recognize characteristic substances (biomarkers), particularly those with a low concentration, in spatially resolved mass spectra or mobility spectra and to determine their signal strength. This is one reason why the classification quality of tissue states in state maps calculated according to the prior art is lower than a classification from homogenized tissue samples. Various types of assignment error occur with every type of classification, including the determination of tissue states. These errors lead to statistical parameters which specify the quality of the classification.

The objective of the invention is to provide a method for the determination and visualization of the spatial distribution of tissue states of a tissue sample, in which the determination of the spatially resolved tissue states has a better classification quality than the Prior Art.

SUMMARY OF THE INVENTION

The present invention provides a method for the determination and visualization of the spatial distribution of tissue states of a tissue sample, wherein
 a mass/mobility map is acquired at each of a plurality of sample sites of the tissue sample,
 at each sample site, signal heights are determined at characteristic signal positions in the corresponding mass/mobility map, from which a tissue state is calculated for each sample site with the aid of a mathematical/statistical classification algorithm; and
 the spatial distribution of the tissue states calculated for the sample sites is represented graphically.

The number of characteristic signal positions used to calculate the tissue states is preferably less than 5, 10, 20, 50 or 100. The number of different tissue states (classes) can be 2, 3, 4 or 5, for example. At each sample site, it is also possible for more than one mass/mobility map to be acquired. A mass/mobility map is particularly formed by plotting the ion mobility as a function of the ion mass. The mathematical/statistical classification algorithm can comprise a principal component analysis (PCA), a genetic algorithm (GA, a linear discriminant analysis (LDA), a support vector machine (SVM), a support vector regression (SVR), a neuronal network (NN), or a learning vector quantification (LVQ).

The sample sites can substantially cover the whole tissue sample or only a straight or curved line on the tissue sample. The sample sites can cover a real subarea or several subareas which are separated from each other on the tissue sample. A user can specify the sample sites at which a mass/mobility map is to be acquired on an optical image of a second tissue sample whose tissue type corresponds to the tissue type of the sample under investigation or originates from a neighboring sampling location in the tissue.

It is preferable for the spatial distribution of the calculated tissue states to be represented graphically by brightness levels or false colors. The graphic representation of the spatial distribution of the calculated tissue states can particularly be laid under an optical image of the tissue sample, particularly a microscopy image with higher spatial resolution wherein the tissue sample is preferably stained only after the mass/mobility maps have been acquired and the optical image is preferably taken of the stained tissue sample.

The tissue sample is preferably a tissue section fixed with formalin and embedded in paraffin (FFPE) after renaturing (antigen retrieval); a fresh, frozen tissue section; an imprint of a tissue section; or one of the sample areas on a Tissue Microarray (TMA) after renaturing (antigen retrieval). It is also possible to analyze several tissue samples in the form of neighboring tissue sections, with the spatial distribution of the calculated tissue states of the tissue samples being displayed in three dimensions.

The (ionic) signals at the characteristic signal positions originate from at least two chemically distinguishable substances, particularly from isomeric substances with the same empirical formula. Different substance classes, such as peptides, glycans and lipids, are at least partially separated in a mass/mobility map and the at least two chemically distinguishable substances preferably originate from one of the substance classes. The peptides can be generated at least partially by an enzymatic digest of the proteins of the tissue sample, in particular by means of a trypsin preparation of the histological sample before the mass/mobility map is acquired. The glycans can be generated at least partially by a deglycolyzation of glycoproteins of the tissue sample, particularly by means of a PNGase preparation of the histological sample before the mass/mobility maps are acquired.

There are different ways to select and determine the characteristic signal positions.

In a first preferred embodiment, a mass/mobility map is acquired at each of a plurality of sample sites of a tissue sample of similar type, wherein the tissue state for at least some of the sample sites of the tissue sample of similar type, and hence for the corresponding mass/mobility map, is known. Signal heights are determined at a first signal position in the mass/mobility maps with known tissue state and assigned to the particular known tissue state. The first signal position becomes one of the characteristic signal positions if the tissue states are sufficiently distinguishable via the distribution of the signal heights at the first signal position (univariate statistical analysis). This univariate statistical analysis is furthermore conducted at a large number of further signal positions. It is preferable to use more than one tissue sample of similar type for the univariate analysis.

In a second preferred embodiment, the tissue state for at least some of the sample sites of the tissue sample under investigation, and hence for the corresponding mass/mobility maps, is known. The signal heights are determined at a first signal position in the mass/mobility maps with known tissue state and assigned to the particular known tissue state. The first signal position becomes one of the characteristic signal positions if the tissue states are sufficiently distinguishable via the distribution of the signal heights at the first signal position (univariate statistical analysis). This univariate statistical analysis is furthermore conducted at a large number of further signal positions.

In both embodiments, a receiver operating characteristic curve (ROC curve) can be generated in the univariate statistical analysis for each signal position analyzed. A signal position becomes one of the characteristic signal positions if the area under the receiver characteristic curve is larger than a specified limit value, in particular larger than 0.6, 0.7, 0.8 or 0.9.

The signal positions determined as being characteristic and the corresponding signal heights are preferably used to train a supervised classification algorithm. One or more signal positions which were determined to be characteristic can be removed in the course of the training.

In a third preferred embodiment, either a mass/mobility map is acquired at each of a plurality of sample sites of at least one tissue sample, with the tissue state being known for at least some of the sample sites of the at least one tissue sample, or the tissue state is known for at least some of the sample sites of the tissue sample under investigation itself. If more than one tissue sample is used, the samples should be of the same type. The signal heights are determined at a plurality of signal positions in the mass/mobility maps with known tissue state and used together with the known tissue states for each position to train a supervised classification algorithm, wherein the characteristic signal positions are determined only in the course of the training.

The mass/mobility maps are preferably acquired with a mass spectrometric system which comprises a trapped ion mobility separator (TIMS separator, TIMS=Trapped Ion Mobility Spectrometry) and a mass analyzer. The mass analyzer can be a time-of-flight mass analyzer, particularly with orthogonal ion injection (OTOF), an electrostatic ion trap, an RF ion trap, an ion cyclotron resonance ion trap or a quadrupole mass filter.

A typical mode of operation of a TIMS separator is that a gas flow drives ions under investigation against a ramp of a counteracting electrical field barrier so that the ions are trapped at positions along the ramp according to their mobility. After ions have been supplied, a further inflow of ions is stopped and the height of the counteracting electric field barrier is steadily decreased so that ion species can pass through the electric field barrier in the order of their mobility. A TIMS separator is usually operated in the low-pressure region from 2 to 500 Pa and uses an electric RF field for the radial confinement of the ions. TIMS separators are described in the U.S. Pat. No. 6,630,662 (Loboda) and U.S. Pat. No. 7,838,826 (Park), for example, and the theoretical foundations can be found in the paper "Fundamentals of Trapped Ion Mobility Spectrometry" by Michelmann et al. (J. Am. Soc. Mass Spectrom., 2015, 26, 14-24).

The TIMS separator can be operated in a temporal zoom mode, wherein the instantaneous scan speed of the TIMS separator is reduced at each mobility position of the characteristic signal positions, thereby increasing the mobility resolution there. The TIMS separator preferably comprises an additional trapping region, which is spatially separate from and upstream of the separation region, and is operated in a mode of operation with parallel accumulation. In this mode of operation, ions of a sample site are accumulated in the additional trapping region, while in the separation region, previously accumulated ions of a different sample site are separated according to mobility to acquire a mass/mobility map. This means that more than 5, 10, 20, 50 or 100 mass/mobility maps can be acquired per second.

In a method according to the invention, the tissue sample is preferably prepared on a sample support, wherein the ions are generated at the sample sites by a spatially resolving ion source, particularly by means of ionization by matrix-assisted laser desorption (MALDI), desorption electrospray ionization (DESI), matrix assisted laser desorption electrospray ionization (MALDESI) or laser desorption with subsequent chemical ionization (LDCI).

The present invention provides a further method for the determination and visualization of the spatial distribution of tissue states of a tissue sample, wherein a plurality of mass/mobility maps is loaded into an electronic data processing system, with each mass/mobility map being assigned to a sample site of the tissue sample;

for each mass/mobility map, signal heights are determined at characteristic signal positions, from which a tissue state is calculated for the assigned sample site with the aid of a mathematical/statistical classification algorithm; and the spatial distribution of the tissue states calculated for the sample sites is represented graphically.

Compared to the known methods of imaging mass spectrometry, in the method according to the invention, biomarkers are no longer signals in spatially resolved one-dimensional mass spectra or mobility spectra, but signals in spatially resolved two-dimensional mass/mobility maps. The acquisition of a mass/mobility map at each sample site corresponds to the known mass spectrometric analysis of a homogenized tissue sample with prior separation method in as far as the mobility separation in the gaseous phase replaces the separation process in the liquid, and a better classification quality for individual sample sites is thus achieved.

The mobility separation improves, or indeed enables, the ability to distinguish between substances that are characteristic of a tissue state and the plurality of substances that are not characteristic. In particular, the use of mass/mobility maps allows characteristic isomers to be distinguished from non-characteristic isomers, since only then can these characteristic isomers be used for calculation of tissue states. Mobility separation, moreover, lowers the demand placed on the resolving power of the mass analyzer, as separation of the substances is carried out in two dimensions and does not have to be completely achieved in the mass spectrum.

A MALDI TOF mass analyzer with axial ion injection (ATOF) is usually used in imaging mass spectrometry. Typically, between 1,000 and 10,000 mass spectra per second are acquired, and around 100 individual mass spectra per sample site are summed to form a sum spectrum. This means that typically between 10 and 100 sample sites per second can be analyzed with an ATOF mass analyzer without mobility separation. It is surprising that the number of sample sites which can be analyzed per second when a mass/mobility map is acquired does not change substantially if the mass/mobility map is acquired with a mass spectrometric system which comprises firstly a TIMS separator with an additional trapping region and secondly a mass analyzer with a sufficiently high spectral acquisition rate, such as an OTOF mass analyzer. The TIMS separator is preferably operated in the operating mode with parallel accumulation and a separation rate of between 10 and 100 Hz.

A further advantage of the TIMS-OTOF system, compared to the ATOF mass analyzer, is that acquisition of the mass spectra in the OTOF mass analyzer is decoupled from the ionization, i.e. the ionization can be performed with a higher repetition rate than the spectral acquisition, for example. A higher repetition rate of the ionization process allows the tissue sample to be completely consumed in the time allocated for analysis of the sample site, and allows optimum laser pulse energies to be used for the MALDI ionization, in particular. This results in more ions and a better signal-to-noise ratio particularly for substances at low concentration.

The mass spectrometric system can additionally comprise a mass filter and a fragmentation cell between the TIMS separator and the mass analyzer so that selected ion species can be analyzed by means of tandem mass spectrometry. A preferred embodiment of the invention comprises fragmenting the ions, which are separated according to mobility, and analyzing the fragment ions by means of data-independent analysis (DIA). This results in a three-dimensional parent mass-fragment mass mass/mobility map at each sample site, which is used to calculate the tissue states.

DETAILED DESCRIPTION

Although the present invention is described in various embodiments, it is possible to combine features and modifications in form and detail without deviating from the scope of the invention defined by the attached claims. The invention can be better understood by referring to the following drawings. The elements in the illustrations are not necessarily to scale, but are primarily intended to illustrate the principles of the invention (mostly schematically).

Figure 1A:
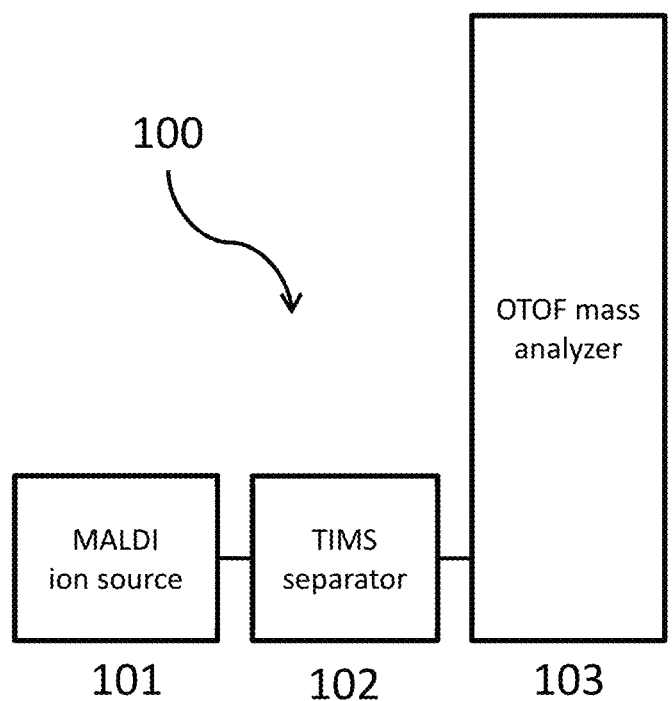
FIG. 1A shows a schematic representation of a preferred mass spectrometric system (100) to perform a method according to the invention, which has a MALDI ion source (101), a TIMS separator (102) and an OTOF mass analyzer (103).

FIG. 1A shows a schematic representation of a preferred mass spectrometric system (100) to perform a method according to the invention, which has a MALDI ion source (101), a TIMS separator (102) and an OTOF mass analyzer (103).

Figure 1B:
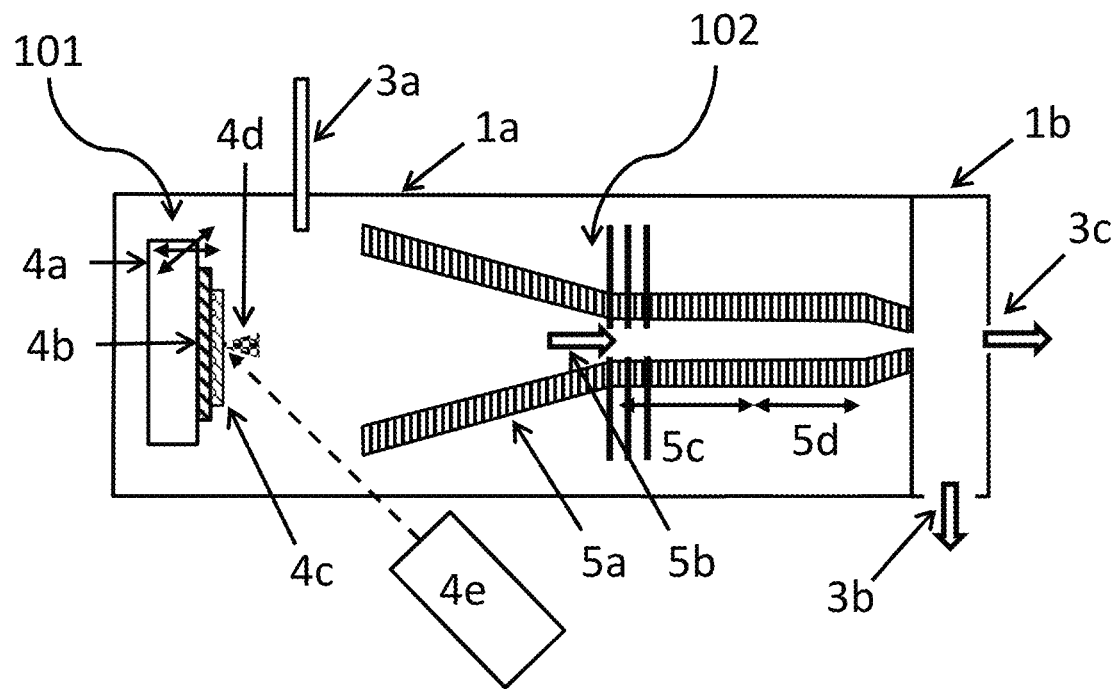
FIG. 1B shows more details of the MALDI ion source (101) and the TIMS separator (102).

FIG. 1B shows more details of the MALDI ion source (101) and the TIMS separator (102) in an example embodiment.

The MALDI ion source (101) and the TIMS separator (102) are located in the vacuum chamber (1a), which is maintained at a pressure of 200 Pa. Gas is fed into the vacuum chamber (1a) via a capillary (3a) and pumped off at the exit of the TIMS separator (102) via the adjacent vacuum chamber (1b) at the pump connection (3b) and at the exit (3c).

The MALDI ion source (101) has an x-y translation stage (4a), a sample support (4b), a prepared tissue sample (4c) and a laser system (4e). The laser system (4e) focuses a laser pulse onto the prepared tissue sample (4c) and generates ions (4d) from a 10-micrometer spot on the prepared tissue sample (4c). The x-y translation stage (4a) moves the sample sites of the prepared tissue sample (4c) into the focus of the laser system (4e) one after the other (raster scanning method).

The TIMS separator (102) comprises an RF ion funnel (5a), a trapping region (5c) and a separation region (5d).

The RF ion funnel (5a) is a quadrupolar RF ion funnel and is constructed from a stack of segmented electrodes provided with apertures. Each electrode comprises four segments. The apertures of the electrodes taper to smaller diameters and thus form an interior volume in the shape of a funnel. The two phases of an RF voltage are applied alternately to adjacent segments of each individual electrode and to adjacent segments of neighboring electrodes. The RF field generates a pseudopotential, which collects the ions (4d) generated in the MALDI ion source (101) and keeps them away from the inner wall of the RF funnel. The RF field of the quadrupolar RF ion funnel (5a) allows a continuous transition to the RF field of the trapping region (5c).

The ions are driven into the trapping region (5c) of the TIMS separator (102) by the gas flow (5b). The gas flow (5b) is generated by gas being pumped out of the vacuum chamber (1a) and has a speed of around 100 m/s.

The trapping region (5c) and the separation region (5d) are both constructed as segmented linear RF quadrupoles. The TIMS separator (102) is operated in parallel accumulation mode, i.e. the TIMS separator (102) accumulates ions in the trapping region (5c), while previously accumulated ions are being analyzed in the separation region (5d) at the same time. The gas flow (5b) drives ions emerging from the RF funnel (5a) against a ramp of a counteracting electric field barrier of the trapping region (5c) so that the ions are trapped axially along the ramp at positions which correspond to their mobility. While ions are accumulating in the trapping region (5c), the gas flow (5b) also drives ions collected in a previous accumulation and transferred into the separation region (5d) against a ramp of a counteracting electric field barrier of the separation region (5d) so that the ions are axially confined and spatially separated according to their mobility. After the separation region (5d) has been filled with ions under investigation, the height of the counteracting electric field barrier is steadily reduced so that ion species are released from the separation region (5d) in the order of their mobility.

The separation process takes 50 milliseconds, for example, in which time the OTOF mass analyzer acquires a mass/mobility map comprising 500 mass spectra at a spectral acquisition rate of 10 kHz.

Figure 2A:
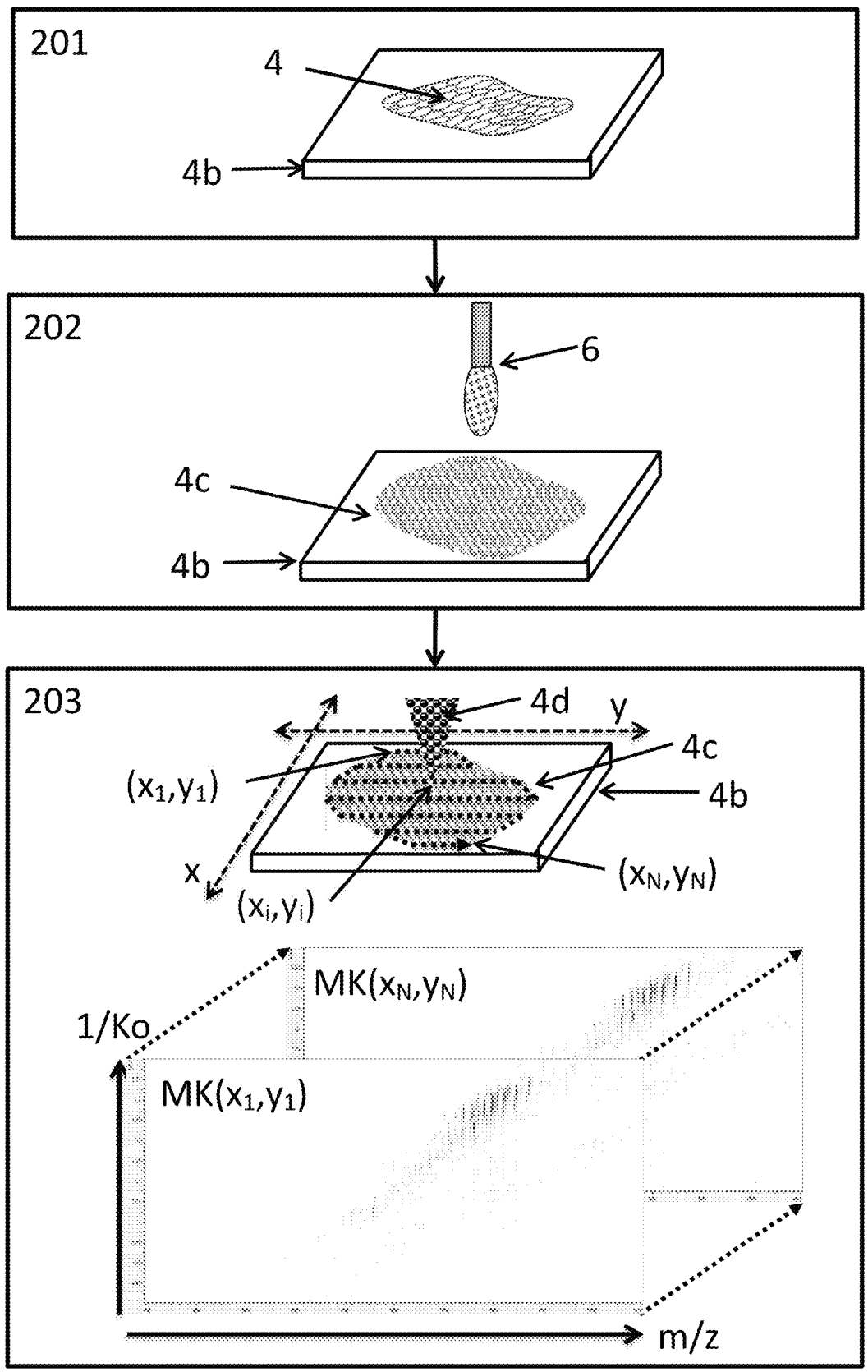
FIGS. 2A and 2B show a flowchart of a first method according to the invention, with the steps (201) to (206).
Figure 2B:
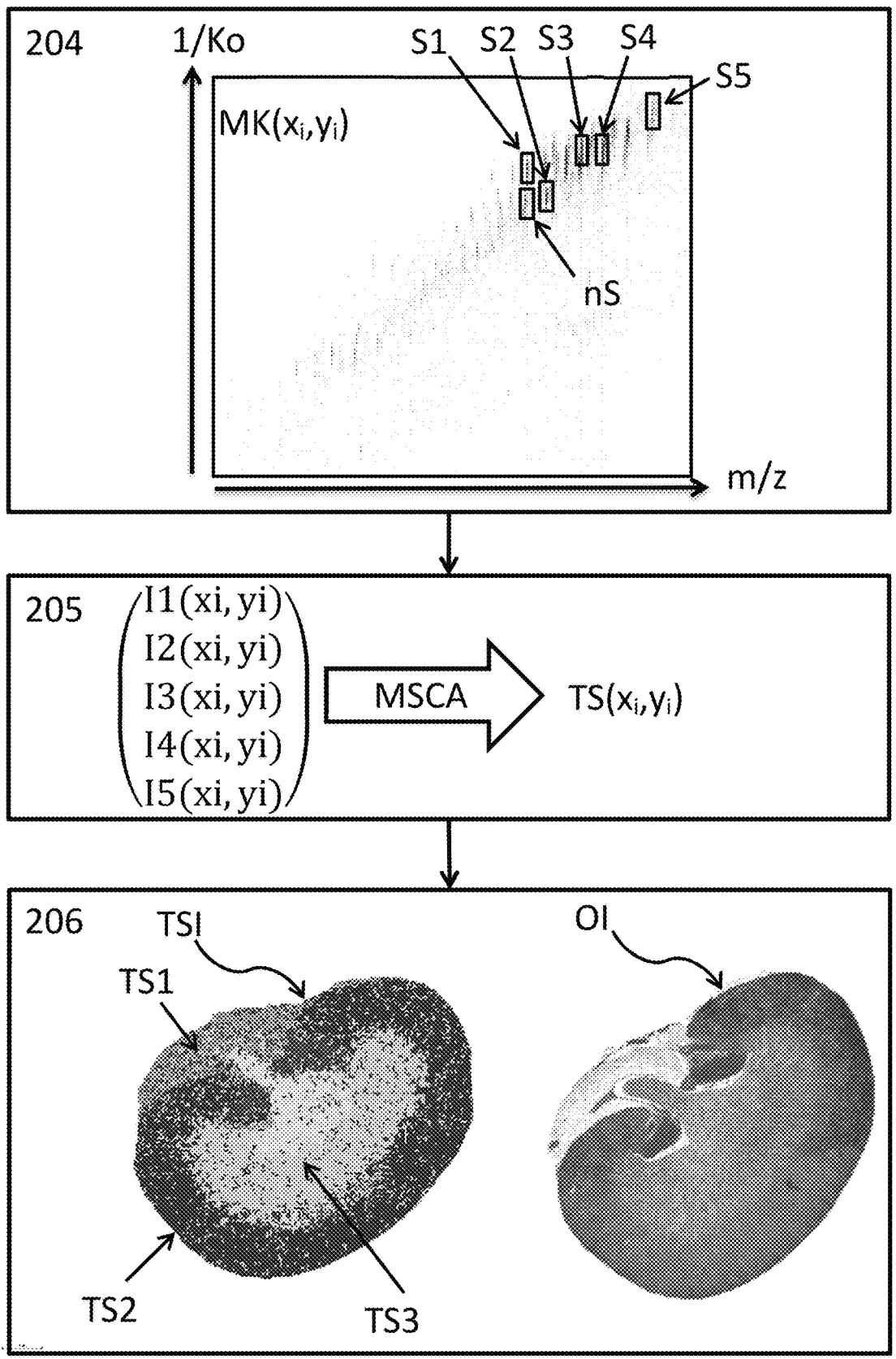

FIGS. 2A and 2B show a flowchart of a first method according to the invention in an embodiment with the steps (201) to (206).

In method step 201 a tissue section (4) under investigation is applied to a sample sup-port (4b), which has an electrically conductive surface. To this end, the tissue is first stabilized by freezing and cut with a microtome (not shown) into several tissue sections around ten micrometers thick.

In method step (202), a piezo-sprayer (6) is used to apply a matrix layer to the tissue section (4), and a prepared tissue section (4c) is produced. The methods and devices which should preferably be used for this purpose can be found in the patent specifications DE 10 2006 019 530 B4 and DE 10 2006 059 695 B3, for example.

In method step (203), the prepared tissue section (4c) is scanned in the x and y directions with laser pulses of a focused laser beam. To get from one sample site to the next, the sample support (4b) is shifted along the x and y axis using a movement device which is not shown. Each sample site $(x_i,y_i)$ is irradiated around several hundred times. The ions (4d) generated in the individual MALDI processes are temporarily stored in the trapping region of a TIMS separator before being separated temporally according to their mobility. The temporally separated ions are analyzed in an OTOF mass analyzer so that a spatially resolved mass/mobility map $MK(x_i,y_i)$ is assigned to each sample site $(x_i,y_i)$.

In method step (204), the signal heights at the characteristic signal positions (S1) to (S5) are determined for each mass/mobility map $MK(x_i,y_i)$. The characteristic signal position (S1) is separated from a non-characteristic signal position (nS) by the additional mobility separation. If a two-dimensional mass/mobility map were not used, it would be difficult or impossible to distinguish the signals at the characteristic signal position (S1) and at the non-characteristic position (nS), and the quality of the classification would be lower.

In method step (205), a mathematical/statistical classification algorithm (MSCA) is used to calculate the tissue state $TS(x_i,y_i)$ at the sample site $(x_i,y_i)$ from the signal heights (I1)-(I5) determined at the characteristic signal positions (S1)-(S5).

In method step (206), the spatial distribution of the tissue states $TS(x_i,y_i)$ calculated at the sample sites $(x_i,y_i)$ is graphically represented as a tissue state image (TSI), in which three tissue states (TS1), (TS2) and (TS3) are present. By way of comparison, an optical image (OI) of the same tissue sample is shown, which is recorded after the matrix layer has been removed and after staining.

Figure 3:
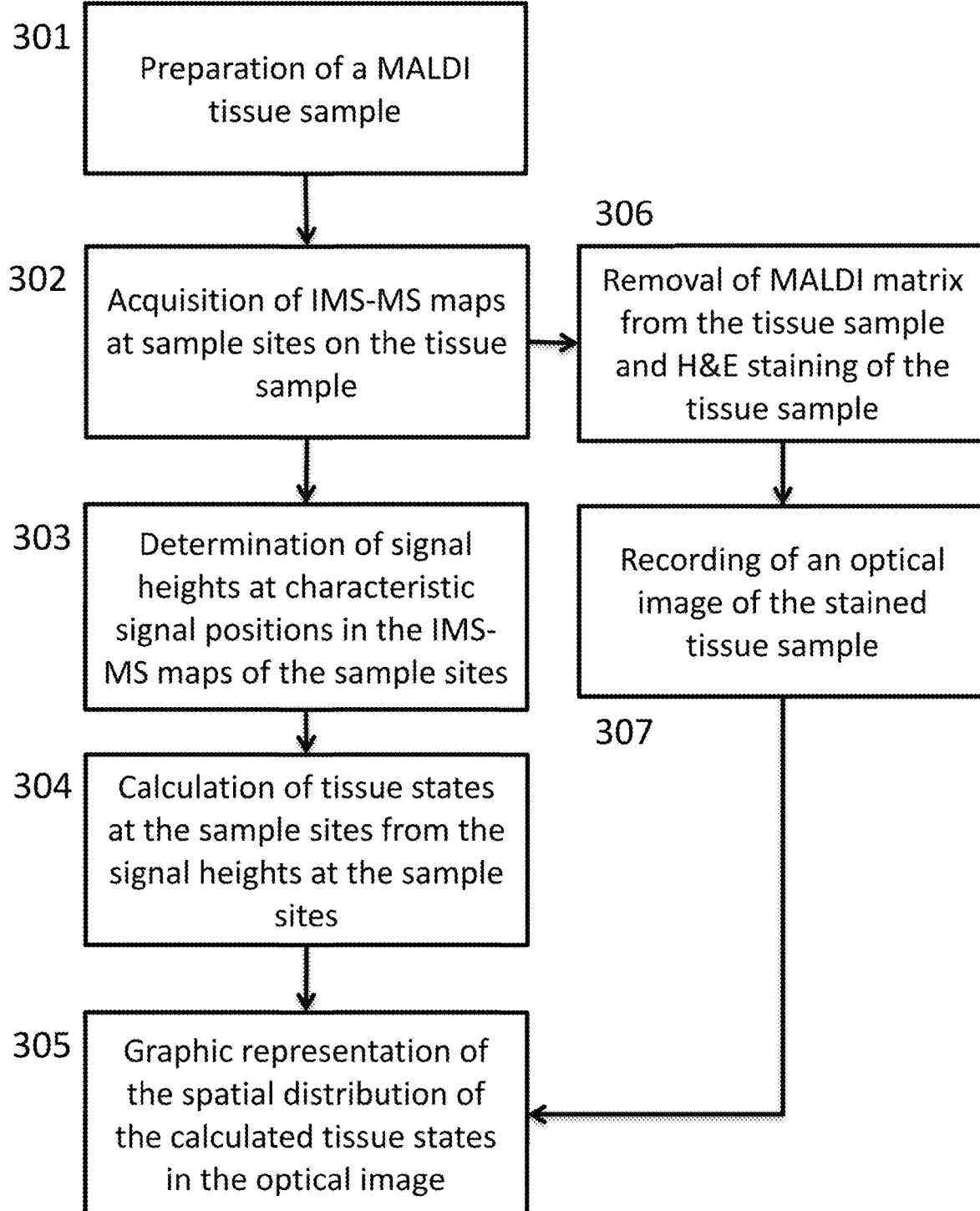
FIG. 3 shows a schematic flowchart of a second method according to the invention, with the steps (301) to (307).

FIG. 3 shows a schematic flowchart of a second method according to the invention in an embodiment with the steps (301) to (307). In method step (301), a MALDI tissue sample is prepared. In method step (302), mass/mobility maps are acquired at the sample sites of the tissue sample. In method step (303), signal heights at characteristic signal positions in the mass/mobility maps are determined, and in method step (304) they are used to calculate the tissue states. After the mass/mobility maps have been acquired in method step (302), the matrix is removed from the prepared tissue sample, and the tissue sample is subjected to H&E staining in method step (306). In method step (307), an optical image of the stained tissue sample is recorded. In the final method step (305), the spatial distribution of the tissue states calculated in method step (304) are represented graphically in the optical image.

Figure 4:
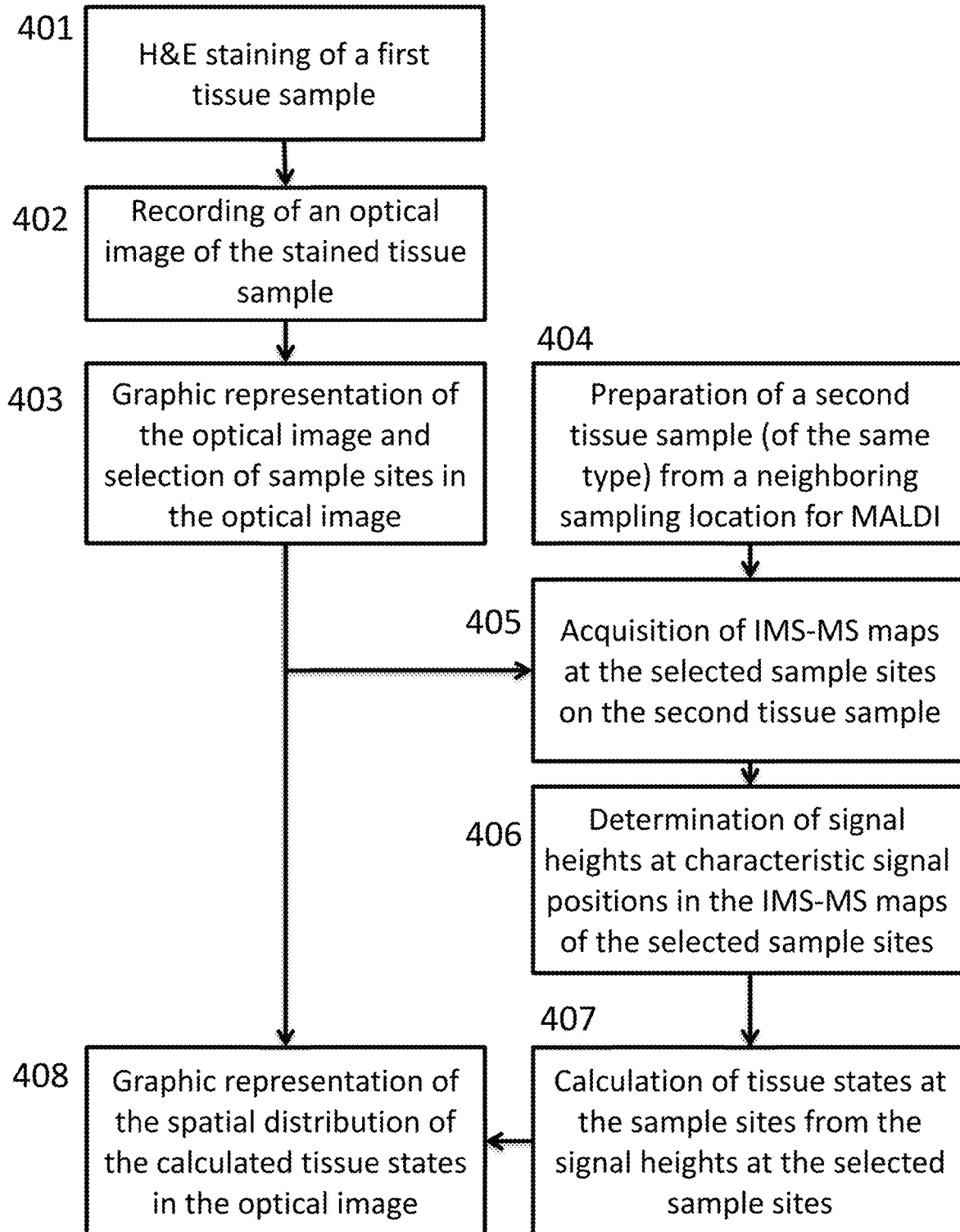
FIG. 4 shows a schematic flowchart of a third method according to the invention, with the steps (401) to (408).

FIG. 4 shows a schematic flowchart of a third method according to the invention in an embodiment with the steps (401) to (408). In method step (401), a first tissue sample is H&E stained. In method step (402), an optical image of the stained tissue sample is recorded. In method step (403), the optical image is graphically represented, and sample sites are selected in the optical image. Parallel to recording the optical image, a second tissue sample of the same type from a neighboring sampling location is prepared as a MALDI tissue sample in method step (404). After selection of sample sites in method step (403), mass/mobility maps are acquired at the selected sample sites in method step (405). In method step (406), signal heights at characteristic signal positions in the mass/mobility maps of the selected sample sites are determined and used to calculate the tissue states at the selected sample sites in method step (407). In the final method step (408), the spatial distribution of the tissue states calculated in method step (407) are represented graphically in the optical image.

The invention claimed is:

1. A method for the determination and visualization of the spatial distribution of tissue states of a tissue sample, the method comprising:
   acquiring a mass/mobility map indicative of ion mobility as a function of ion mass at each of a plurality of sample sites of the tissue sample;
   determining, at each sample site, signal heights at characteristic signal positions in the corresponding mass/mobility map;
   determining, using said signal heights, a tissue state for each sample site using one or more reference sample sites of reference tissue whose tissue states are known; and
   representing graphically the spatial distribution of the tissue states calculated for the sample sites.

2. The method according to claim 1 further comprising providing, as the tissue sample, a formalin-fixed paraffin-embedded (FFPE) tissue section after renaturing; a fresh, frozen tissue section; an imprint of a tissue section; or one of a plurality of sample areas on a Tissue Microarray (TMA) after renaturing.

3. The method according to claim 1, wherein determining, at each sample site, signal heights at characteristic signal positions in the corresponding mass/mobility map comprises determining said signal heights for signals that originate from at least two chemically distinguishable substances and from two isomeric substances with the same empirical formula.

4. The method according to claim 3, wherein the method further comprises separating different substance classes at least partially in the mass/mobility maps, and wherein the two or more chemically distinguishable substances originate from one substance class.

5. The method according to claim 4, wherein separating different substance classes at least partially in the mass/mobility map comprises separating substance classes that encompass peptides, glycans and/or lipids.

6. The method according to claim 5, wherein separating substance classes that encompass peptides, glycans and/or lipids comprises separating peptides produced at least partially by an enzymatic digest of the proteins of the tissue sample.

7. The method according to claim 5, wherein separating substance classes that encompass peptides, glycans and/or lipids comprises separating glycans produced at least partially by a deglycolyzation of glycoproteins of the tissue sample.

8. The method according to claim 1, wherein the tissue sample is a first tissue sample, and wherein the method further comprises:
   (a) acquiring a mass/mobility map at each of a plurality of reference sample sites of a reference tissue sample of a type similar to the first tissue sample, wherein the tissue state for certain predetermined reference sample sites of the reference tissue sample is known;
   (b) determining signal heights at a first signal position in the mass/mobility maps of said predetermined reference sample sites and assigning the signal heights determined at the first signal position to said known tissue state, such that the first signal position becomes one of said characteristic signal positions; and (c) repeating step (a) for signal positions in the mass/mobility maps of said predetermined reference sample sites other than the first signal position.

9. The method according to claim 8, wherein a receiver operating characteristic curve is generated in a univariate statistical analysis for each signal position analyzed, and an analyzed signal position becomes one of the characteristic signal positions if an area under the receiver operating characteristic curve is larger than a specified limit value.

10. The method according to claim 8 further comprising distinguishing said known tissue state from another one of said tissue states via a distribution of signal heights at the first signal position.

11. The method according to claim 1, wherein the tissue state for certain predetermined sample sites of the tissue sample under investigation, and hence for the corresponding mass/mobility maps, is known, thus establishing the reference sample sites in reference tissue, and wherein the method further comprises:
   (a) determining signal heights at a first signal position in the mass/mobility maps of said predetermined sample sites and assigning said signal heights determined at the first signal position to said known tissue state, such that the first signal position becomes one of said characteristic signal positions; and
   (b) repeating step (a) for signal positions in the mass/mobility maps of said predetermined sample sites other than the first signal position.

12. The method according to claim 11, wherein a receiver operating characteristic curve is generated in a univariate statistical analysis for each signal position analyzed, and an analyzed signal position becomes one of the characteristic signal positions if an area under the receiver operating characteristic curve is larger than a specified limit value.

13. The method according to claim 11 further comprising distinguishing said known tissue state from another one of said tissue states via a distribution of signal heights at the first signal position.

14. The method according to claim 1, wherein acquiring a mass/mobility map at each of a plurality of sample sites comprises acquiring said mass/mobility maps with a mass spectrometric system which comprises a trapped ion mobility separator (TIMS separator) and a mass analyzer.

15. The method according to claim 14, wherein acquiring said mass/mobility maps with a mass spectrometric system which comprises a trapped ion mobility separator and a mass analyzer comprises acquiring said mass/mobility maps with a mass spectrometric system which comprises a trapped ion mobility separator that has a trapping region, which is spatially separate and upstream of the separation region, and that is operated in a mode of operation with parallel accumulation.

16. The method according to claim 15, wherein acquiring said mass/mobility maps with a mass spectrometric system which comprises a trapped ion mobility separator that is operated in a mode of operation with parallel accumulation comprises accumulating ions of a sample site in the additional trapping region while a mass/mobility map of previously accumulated ions of a different sample site is being acquired.

17. The method according to claim 1, wherein the tissue state for each sample site is determined using a mathematical/statistical classification algorithm.

18. The method according to claim 17, wherein the mathematical/statistical classification algorithm comprises one from a group including: neural networks, linear vector quantization (LVQ), neural gas (NG), self-organizing map (SOM), support vector machines (SVM), support vector regression (SVR), genetic algorithms for cluster analysis, principal component analysis (PCA), decision trees, nearest neighbor classifiers (k nearest neighbor), and linear discriminant analysis (LDA).

19. A method for the determination and visualization of the spatial distribution of tissue states of a tissue sample, the method comprising:
   acquiring a plurality of mass/mobility maps indicative of ion mobility as a function of ion mass and loading said mass/mobility maps into an electronic data processing system, such that each mass/mobility map is assigned to a sample site of the tissue sample;
   determining, for each mass/mobility map, signal heights at characteristic signal positions;
   determining, using said signal heights, a tissue state for the assigned sample site using one or more reference sample sites of reference tissue whose tissue states are known; and
   representing graphically the spatial distribution of the tissue states calculated for the sample sites.

20. The method according to claim 15, wherein the method further comprises using as mass analyzer a time-of-flight mass analyzer with orthogonal ion injection (OTOF).

* * * * *